(12) United States Patent
Ortigosa et al.

(10) Patent No.: US 10,745,457 B2
(45) Date of Patent: Aug. 18, 2020

(54) PROCESS FOR OBTAINING INSULIN WITH CORRECTLY FORMED DISULFIDE BONDS

(71) Applicant: Merck Sharp & Dohme Corp., Rahway, NJ (US)

(72) Inventors: Allison D. Ortigosa, Harrisonburg, VA (US); Rebecca A. Chmielowski, Clark, NJ (US); Mark C. Sleevi, Longmont, CO (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/755,354

(22) PCT Filed: Aug. 29, 2016

(86) PCT No.: PCT/US2016/049178
§ 371 (c)(1),
(2) Date: Feb. 26, 2018

(87) PCT Pub. No.: WO2017/040363
PCT Pub. Date: Mar. 9, 2017

(65) Prior Publication Data
US 2018/0244744 A1 Aug. 30, 2018

Related U.S. Application Data

(60) Provisional application No. 62/213,159, filed on Sep. 2, 2015.

(51) Int. Cl.
*C07K 14/62* (2006.01)
*A61P 5/48* (2006.01)

(52) U.S. Cl.
CPC ............ *C07K 14/62* (2013.01); *A61P 5/48* (2018.01); *C12Y 304/17002* (2013.01)

(58) Field of Classification Search
CPC .... C07K 14/62; A61P 5/48; C12Y 304/17002
See application file for complete search history.

(56) References Cited

U.S. PATENT DOCUMENTS

| | | |
|---|---|---|
| 4,677,196 A | 6/1987 | Rausch et al. |
| 2007/0106063 A1 | 5/2007 | Rubroeder et al. |
| 2011/0152507 A1* | 6/2011 | Edupuganti ............ C07K 14/62 530/399 |
| 2012/0214965 A1* | 8/2012 | Zimmerman .......... C07K 14/62 530/303 |
| 2014/0315798 A1 | 10/2014 | Stowell et al. |
| 2016/0060291 A1* | 3/2016 | Krishnan ............. C07K 14/535 530/303 |

FOREIGN PATENT DOCUMENTS

| | | |
|---|---|---|
| WO | WO1992004382 | 3/1992 |
| WO | WO2013168178 A1 | 11/2013 |

OTHER PUBLICATIONS

Spencer (Year: 1995).*
Kim, C-K et al, Large-Scale Refolding and Enzyme Reaction of Human Preproinsulin for production of Human Insulin, Journal of Microbiology and Biotechnology, 2015, pp. 1742-1750, vol. 25, No. 10.
Ren, P et al, Bacterial expression of human chorionic gonadotropin [alpha] subunit: studies on refolding, dimer assembly and interaction with two different [beta] subunits, Molecular and Cellular Endocrinology, 1995, pp. 39-51, vol. 113.
Wu, R et al, Expression, refolding and purification of a human interleukin-17A variant, Cytokine, 2011, pp. 107-114, vol. 53, No. 1.

* cited by examiner

Primary Examiner — Rachael E Bredefeld
Assistant Examiner — Ibrahim D Bori
(74) Attorney, Agent, or Firm — John David Reilly; Anna L. Cocuzzo

(57) ABSTRACT

A process for solubilization and refolding of precursor insulin or insulin analogs from inclusion body isolates for use in the production of insulin or insulin analog is described.

16 Claims, 2 Drawing Sheets

Specification includes a Sequence Listing.

SEQUENCE LISTING

<160> NUMBER OF SEQ ID NOS: 6

<210> SEQ ID NO 1
<211> LENGTH: 21
<212> TYPE: PRT
<213> ORGANISM: Homo sapiens

```
<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 102
<212> TYPE: PRT
<213> ORGANISM: Artificial sequence
<220> FEATURE:
<223> OTHER INFORMATION: Precursor insulin glargine

<400> SEQUENCE: 3

Ser Gln Ser Ile Gly Val Phe Val Gln Asp Tyr Asn Ser His Thr Arg
1               5                   10                  15

Phe Val Asn Gln His Leu Cys Gly Ser His Leu Val Glu Ala Leu Tyr
            20                  25                  30

Leu Val Cys Gly Glu Arg Gly Phe Phe Tyr Thr Pro Lys Thr Arg Arg
        35                  40                  45

Glu Ala Glu Asp Leu Gln Val Gly Gln Val Leu Gly Gly Gly Pro
    50                  55                  60

Gly Ala Gly Ser Leu Gln Pro Leu Ala Leu Glu Gly Ser Leu Gln Lys
65                  70                  75                  80

Arg Gly Ile Val Glu Gln Cys Cys Thr Ser Ile Cys Ser Leu Tyr Gln
                85                  90                  95

Leu Glu Asn Tyr Cys Gly
            100

<210> SEQ ID NO 4
<211> LENGTH: 102
<212> TYPE: PRT
<213> ORGANISM: Artificial sequence
<220> FEATURE:
<223> OTHER INFORMATION: Precursor insulin lispro

<400> SEQUENCE: 4

Ser Gln Ser Ile Gly Val Phe Val Gln Asp Tyr Asn Ser His Thr Arg
1               5                   10                  15

Phe Val Asn Gln His Leu Cys Gly Ser His Leu Val Glu Ala Leu Tyr
            20                  25                  30

Leu Val Cys Gly Glu Arg Gly Phe Phe Tyr Thr Lys Pro Thr Arg Arg
        35                  40                  45

Glu Ala Glu Asp Leu Gln Val Gly Gln Val Leu Gly Gly Gly Pro
    50                  55                  60

Gly Ala Gly Ser Leu Gln Pro Leu Ala Leu Glu Gly Ser Leu Gln Lys
65                  70                  75                  80
```

```
Arg Gly Ile Val Glu Gln Cys Cys Thr Ser Ile Cys Ser Leu Tyr Gln
                85                  90                  95

Leu Glu Asn Tyr Cys Asn
            100

<210> SEQ ID NO 5
<211> LENGTH: 21
<212> TYPE: PRT
<213> ORGANISM: Artificial sequence
<220> FEATURE:
<223> OTHER INFORMATION: Insulin glargine A chain

<400> SEQUENCE: 5

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 6
<211> LENGTH: 32
<212> TYPE: PRT
<213> ORGANISM: Artificial sequence
<220> FEATURE:
<223> OTHER INFORMATION: Insulin glargine B chain

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30
```

PROCESS FOR OBTAINING INSULIN WITH CORRECTLY FORMED DISULFIDE BONDS

CROSS REFERENCE TO RELATED APPLICATIONS

This application is a National Stage Application of PCT/US2016/049178 filed Aug. 29, 2016, and claims benefit under 35 U.S.C. 119(e) of U.S. Provisional Application No. 62/213,159, filed Sep. 2, 2015, both of which is incorporated herein in its entirety.

BACKGROUND OF THE INVENTION

(1) Field of the Invention

The present invention relates to a process for solubilization and refolding of precursor insulin or insulin analogs from inclusion body isolates for use in the production of insulin or insulin analog.

(2) Description of Related Art

Human insulin is a protein having two amino acid chains containing altogether 51 amino acid residues. The insulin molecule contains an A chain peptide and a B chain peptide which are bonded together by six cysteine residues forming three disulfide bonds between following positions: A6-A11; A7-B7; and A20-B19. This represents a total of 6 cysteines available for refolding with 15 possible disulfide bond combinations. The correct three-disulfide bond configuration is important in maintaining the native conformation and biological activities of the molecule.

Genetic engineering processes enable human proinsulin or proinsulin which has an amino acid sequence and/or amino acid chain length differing from human insulin to be prepared in microorganisms such as E. coli. However, proinsulins prepared from E. coli cells modified by genetic engineering do not have any correctly linked cystine bridges. Thus, processes have been developed for refolding incorrectly folded proinsulins obtained from microorganisms into correctly folded proinsulins. Process for refolding of proteins have been disclosed in U.S. Published Application Nos. 20040111663; 20050176932; and 20100324269; and WO9918196 and WO9401453. Processes for preparing correctly folded human insulin from human proinsulin have been disclosed in U.S. Pat. Nos. 5,986,048; 6,380,355; 6,727,346, 7,659,363; 6,281,329; 5,952,461; 5,663,291; and 5,473,049; and EP0055945 and EP0037255. Another process for obtaining proinsulin having correctly linked cysteine bridges was disclosed in Biochemistry 60:622-629 (1968).

The present invention provides a process for obtaining insulin having correctly linked cysteine bridges in the insulin amino acid chain, in which fewer process steps are necessary and, all in all, lower purification losses occur.

BRIEF SUMMARY OF THE INVENTION

The present invention provides a process for obtaining a precursor molecule of insulin or insulin analog having correctly bonded cysteine bridges, which comprises: (a) solubilizing a suspension of inclusion bodies obtained from a microbiological host comprising a precursor of insulin or insulin analog having incorrectly bonded cysteine bridges (i.e., incorrectly folded) in an aqueous solution comprising a chaotropic auxiliary, a thiol reducing agent, and an amine base to provide a solubilization solution; (b) diluting the solubilization solution with a refold diluent solution comprising the amine base and cystamine to provide a refold solution; and (c) incubating the refold solution for a time and temperature sufficient to provide the precursor of insulin or insulin analog having correctly bonded cysteine bridges (i.e., correctly folded).

In particular aspects, the chaotropic auxiliary comprises guanidine or guanidine hydrochloride. In particular aspects, the chaotropic auxiliary comprises urea. In particular aspects the chaotropic auxiliary comprises urea at final concentration of about 3.8 to 4.3 M.

In particular aspects, the thiol reducing agent comprises dithiothreitol (DTT). In particular aspects the thiol reducing agent comprises DTT at a concentration of about 2.2 to 2.8 mM. In particular aspects the thiol reducing agent comprises DTT at a concentration of about 2.5 mM.

In particular aspects, solubilization solution comprises the precursor of insulin or insulin analog having incorrectly bonded cysteine bridges at a concentration of about 12 to 18 g/L. In particular aspects, solubilization solution comprises the precursor of insulin or insulin analog having incorrectly bonded cysteine bridges at a concentration of about 15 g/L.

In particular aspects, the solubilization solution comprises a pH of about 10.2 to 11.0.

In particular embodiments the amine base may comprise arginine, tris, or the like. In particular aspects, the amine base comprises ethanolamine. In particular aspects, the amine base comprises ethanolamine at a concentration of about 0.3 to 0.4 M.

In particular aspects the diluent solution comprises about 10 mM of the amine base, which in particular embodiments may comprise ethanolamine. In particular aspects, step (b) comprises diluting the solubilization solution about 10-fold with a diluent solution comprising the amine base, which in particular embodiments may comprise ethanolamine.

In particular aspects, the refold diluent solution comprises cystamine at a predetermined concentration to provide a refold solution that comprises cystamine at about 0.2 to 0.5 mole cystamine per mole of thiol in the precursor molecule.

In particular aspects, the refold diluent solution comprises cystamine at a predetermined concentration to provide a refold solution that comprises a DTT/cystamine redox ratio between 5:1 to 9:1.

In particular aspects, the refold diluent solution comprises cystamine at a predetermined concentration to provide a refold solution that comprises a DTT/cystamine redox ratio of about 6.5:1 for the refold solution.

In particular aspects, the refold diluent solution comprises cystamine at a predetermined concentration to provide a refold solution that comprises about 345 to 404 µM cystamine.

In particular aspects, the refold diluent solution comprises cystamine at a predetermined concentration to provide a refold solution that comprises about 345 µM cystamine.

In particular aspects, step (c) comprises incubating the refold solution for about 5 to 10 hours and at a temperature of about 9° to 11° C.

In particular aspects, the process further comprises reducing the pH of the refold solution comprising the precursor of insulin or insulin analog having correctly bonded cysteine bridges to about pH 9.0 to 9.4. An acid, such as hydrochloric acid, may be used to quench the refold reaction and allow for subsequent purification.

The present invention further provides a process for obtaining an insulin or insulin analog having correctly bonded cysteine bridges, which comprises (a) solubilizing a suspension of inclusion bodies obtained from a microbiological host comprising a precursor of insulin or insulin analog having incorrectly bonded cysteine bridges (i.e., incorrectly folded) in an aqueous solution comprising a chaotropic auxiliary, a thiol reducing agent, and an amine base to provide a solubilization solution; (b) diluting the solubilization solution with a refold diluent solution comprising the amine base and cystamine to provide a refold solution; (c) incubating the refold solution for a time and temperature sufficient to provide a refold solution comprising a precursor of insulin or insulin analog having correctly bonded cysteine bridges; (d) reducing the pH of the refold solution from step (c); (e) reacting the precursor of insulin or insulin analog having correctly bonded cysteine bridges from step (d) with trypsin or a trypsin-like enzyme and optionally additionally with carboxypeptidase B or mixture of the enzymes to provide the insulin or insulin analog having correctly bonded cysteine bridges; and (f) purifying the insulin or insulin analog having correctly bonded cystine bridges to provide insulin or insulin analog having correctly bonded cysteine bridges.

In particular aspects, the chaotropic auxiliary comprises guanidine or guanidine hydrochloride. In particular aspects, the chaotropic auxiliary comprises urea. In particular aspects the chaotropic auxiliary comprises urea at final concentration of about 3.8 to 4.3 M.

In particular aspects, the thiol reducing agent comprises dithiothreitol (DTT). In particular aspects the thiol reducing agent comprises DTT at a concentration of about 2.2 to 2.8 mM. In particular aspects the thiol reducing agent comprises DTT at a concentration of about 2.5 mM.

In particular aspects, solubilization solution comprises the precursor of insulin or insulin analog having incorrectly bonded cysteine bridges at a concentration of about 12 to 18 g/L. In particular aspects, solubilization solution comprises the precursor of insulin or insulin analog having incorrectly bonded cysteine bridges at a concentration of about 15 g/L.

In particular aspects, the solubilization solution comprises a pH of about 10.2 to 11.0.

In particular embodiments the amine base may comprise arginine, tris, or the like. In particular aspects, the amine base comprises ethanolamine. In particular aspects, the amine base comprises ethanolamine at a concentration of about 0.3 to 0.4 M.

In particular aspects the diluent solution comprises about 10 mM of the amine base, which in particular embodiments may comprise ethanolamine. In particular aspects, step (b) comprises diluting the solubilization solution about 10-fold with a diluent solution comprising the amine base, which in particular embodiments may comprise ethanolamine.

In particular aspects, the refold diluent solution comprises cystamine at a predetermined concentration to provide a refold solution that comprises cystamine at about 0.2 to 0.5 mole cystamine per mole of thiol in the precursor molecule.

In particular aspects, the refold diluent solution comprises cystamine at a predetermined concentration to provide a refold solution that comprises a DTT/cystamine redox ratio between 5:1 to 9:1.

In particular aspects, the refold diluent solution comprises cystamine at a predetermined concentration to provide a refold solution that comprises a DTT/cystamine redox ratio of about 6.5:1 for the refold solution.

In particular aspects, the refold diluent solution comprises cystamine at a predetermined concentration to provide a refold solution that comprises about 345 to 404 μM cystamine.

In particular aspects, the refold diluent solution comprises cystamine at a predetermined concentration to provide a refold solution that comprises about 345 μM cystamine.

In particular aspects, step (c) comprises incubating the refold solution for about 5 to 10 hours and at a temperature of about 9° to 11° C.

In particular aspects, step (d) comprises reducing the pH of the refold solution comprising the precursor of insulin or insulin analog having correctly bonded cysteine bridges to about pH 9.0 to 9.4.

In particular aspects, step (e) comprises reacting the precursor insulin or insulin analog having correctly bonded cysteine bridges from step (d) with citraconic anhydride to produce a citraconylated precursor insulin or insulin analog having correctly bonded cysteine bridges and then reacting the citraconylated precursor insulin or insulin analog having correctly bonded cysteine bridges with trypsin or a trypsin-like enzyme and optionally additionally with the carboxypeptidase B or mixture of the enzymes to provide a citraconylated insulin or insulin analog having correctly bonded cysteine bridges.

In particular aspects, step (f) comprises reacting the citraconylated insulin or insulin analog having correctly bonded cysteine bridges with acetic acid and then purifying the insulin or insulin analog having correctly bonded cysteine bridges to provide insulin or insulin analog having correctly bonded cysteine bridges The present invention further provides a process for obtaining an insulin or insulin analog having correctly bonded cysteine bridges, which comprises (a) solubilizing a suspension of inclusion bodies obtained from a microbiological host comprising a precursor of insulin or insulin analog having incorrectly bonded cysteine bridges (i.e., incorrectly folded) in an aqueous solution comprising a chaotropic auxiliary, a thiol reducing agent, and an amine base to provide a solubilization solution; (b) diluting the solubilization solution with a refold diluent solution comprising the amine base and cystamine to provide a refold solution; (c) incubating the refold solution for a time and temperature sufficient to provide a refold solution comprising a precursor of insulin or insulin analog having correctly bonded cysteine bridges; (d) reducing the pH of the refold solution from step (c); (e) isolating the precursor of insulin or insulin analog having correctly bonded cystine bridges by anion exchange chromatography; (f) cleaving the precursor of insulin or insulin analog having correctly bonded cystine bridges from step (e) with trypsin or a trypsin-like enzyme and optionally additionally with carboxypeptidase B or mixture of the enzymes to provide the insulin or insulin analog having correctly bonded cystine bridges; and (g) purifying the insulin or insulin analog having correctly bonded cystine bridges insulin or insulin analog having correctly bonded cysteine bridges.

In particular aspects, the chaotropic auxiliary comprises guanidine or guanidine hydrochloride. In particular aspects, the chaotropic auxiliary comprises urea. In particular aspects the chaotropic auxiliary comprises urea at final concentration of about 3.8 to 4.3 M.

In particular aspects, the thiol reducing agent comprises dithiothreitol (DTT). In particular aspects the thiol reducing agent comprises DTT at a concentration of about 2.2 to 2.8 mM. In particular aspects the thiol reducing agent comprises DTT at a concentration of about 2.5 mM.

In particular aspects, solubilization solution comprises the precursor of insulin or insulin analog having incorrectly bonded cysteine bridges at a concentration of about 12 to 18 g/L. In particular aspects, solubilization solution comprises the precursor of insulin or insulin analog having incorrectly bonded cysteine bridges at a concentration of about 15 g/L.

In particular aspects, the solubilization solution comprises a pH of about 10.2 to 11.0.

In particular embodiments the amine base may comprise arginine, tris, or the like. In particular aspects, the amine base comprises ethanolamine. In particular aspects, the amine base comprises ethanolamine at a concentration of about 0.3 to 0.4 M.

In particular aspects the diluent solution comprises about 10 mM of the amine base, which in particular embodiments may comprise ethanolamine. In particular aspects, step (b) comprises diluting the solubilization solution about 10-fold with a diluent solution comprising the amine base, which in particular embodiments may comprise ethanolamine.

In particular aspects, the refold diluent solution comprises cystamine at a predetermined concentration to provide a refold solution that comprises cystamine at about 0.2 to 0.5 mole cystamine per mole of thiol in the precursor molecule.

In particular aspects, the refold diluent solution comprises cystamine at a predetermined concentration to provide a refold solution that comprises a DTT/cystamine redox ratio between 5:1 to 9:1.

In particular aspects, the refold diluent solution comprises cystamine at a predetermined concentration to provide a refold solution that comprises a DTT/cystamine redox ratio of about 6.5:1 for the refold solution.

In particular aspects, the refold diluent solution comprises cystamine at a predetermined concentration to provide a refold solution that comprises about 345 to 404 µM cystamine.

In particular aspects, the refold diluent solution comprises cystamine at a predetermined concentration to provide a refold solution that comprises about 345 µM cystamine.

In particular aspects, step (c) comprises incubating the refold solution for about 5 to 10 hours and at a temperature of about 9° to 11° C.

In particular aspects, step (d) comprises reducing the pH of the refold solution comprising the precursor of insulin or insulin analog having correctly bonded cysteine bridges to about pH 9.0 to 9.4.

In particular aspects, step (f) comprises reacting the precursor insulin or insulin analog having correctly bonded cysteine bridges from step (e) with citraconic anhydride to produce a citraconylated precursor insulin or insulin analog having correctly bonded cysteine bridges and then reacting the citraconylated precursor insulin or insulin analog having correctly bonded cysteine bridges with trypsin or a trypsin-like enzyme and optionally additionally with the carboxypeptidase B or mixture of the enzymes to provide a citraconylated insulin or insulin analog having correctly bonded cysteine bridges.

In particular aspects, step (g) comprises reacting the citraconylated insulin or insulin analog having correctly bonded cysteine bridges with acetic acid and then purifying the insulin or insulin analog having correctly bonded cysteine bridges to provide insulin or insulin analog having correctly bonded cysteine bridges.

In a further embodiment, the present invention provides a process for obtaining a precursor molecule of insulin or insulin analog having correctly bonded cysteine bridges, which comprises: (a) solubilizing a suspension of inclusion bodies obtained from a microbiological host comprising a precursor of insulin or insulin analog having incorrectly bonded cysteine bridges in an aqueous solution comprising a chaotropic auxiliary, dithiothreitol (DTT), and an amine base to provide a solubilization solution comprising about 3.8 to 4.3 M of a chaotropic auxiliary, about 2.2 to 2.8 mM DTT, about 0.3 to 0.4 M of an amine base, about 12 to 18 g/L of the precursor of insulin or insulin analog having incorrectly bonded cysteine bridges, and at a pH of about 10.2 to 11.0; (b) diluting the solubilization solution about 10-fold with a refold diluent solution comprising the amine base and cystamine to the diluted solubilization solution to provide a refold solution; and (c) incubating the refold solution for a time and temperature sufficient to provide the precursor of insulin or insulin analog having correctly bonded cysteine bridges.

In particular aspects, the chaotropic auxiliary comprises guanidine or guanidine hydrochloride. In particular aspects, the chaotropic auxiliary comprises urea.

In particular embodiments the amine base may comprise arginine, tris, or the like. In particular aspects, the amine base is ethanolamine. In particular aspects, the diluent solution comprises about 10 mM of the amine base.

In particular aspects, the refold diluent solution comprises cystamine at a predetermined concentration to provide a refold solution that comprises cystamine at about 0.2 to 0.5 mole cystamine per mole of thiol in the precursor molecule.

In particular aspects, the refold diluent solution comprises cystamine at a predetermined concentration to provide a refold solution that comprises a DTT/cystamine redox ratio between 5:1 to 9:1.

In particular aspects, the refold diluent solution comprises cystamine at a predetermined concentration to provide a refold solution that comprises a DTT/cystamine redox ratio of about 6.5:1 for the refold solution.

In particular aspects, the refold diluent solution comprises cystamine at a predetermined concentration to provide a refold solution that comprises about 345 to 404 µM cystamine.

In particular aspects, the refold diluent solution comprises cystamine at a predetermined concentration to provide a refold solution that comprises about 345 µM cystamine.

In particular aspects, step (c) comprises incubating the refold solution for about 5 to 10 hours and at a temperature of about 9° to 11° C.

In particular aspects, the process further comprises reducing the pH of the refold solution comprising the precursor of insulin or insulin analog having correctly bonded cysteine bridges to about pH 9.0 to 9.4. An acid, such as hydrochloric acid, may be used to quench the refold reaction and allow for subsequent purification.

The present invention further provides a process for obtaining an insulin or insulin analog having correctly bonded cysteine bridges, which comprises (a) solubilizing a suspension of inclusion bodies obtained from a microbiological host comprising a precursor of insulin or insulin analog having incorrectly bonded cysteine bridges in an aqueous solution comprising a chaotropic auxiliary, dithiothreitol (DTT), and an amine base to provide a solubilization solution comprising about 3.8 to 4.3 M of a chaotropic auxiliary, about 2.2 to 2.8 mM DTT, about 0.3 to 0.4 M of an amine base, about 12 to 18 g/L of the precursor of insulin or insulin analog having incorrectly bonded cysteine bridges, and at a pH of about 10.2 to 11.0; (b) diluting the solubilization solution about 10-fold with a refold diluent solution comprising the amine base and cystamine to the diluted solubilization solution to provide a refold solution; (c) incubating the refold solution for a time and temperature sufficient to provide a refold solution. comprising the precursor of insulin or insulin analog having correctly bonded cysteine bridges; (d) reducing the pH of the refold solution from step (c); (e) reacting the precursor of insulin or insulin analog having correctly bonded cysteine bridges from step (d) with trypsin or a trypsin-like enzyme and optionally additionally with carboxypeptidase B or mixture of the enzymes to provide the insulin or insulin analog having correctly bonded cysteine bridges; and (f) purifying the insulin or insulin analog having correctly bonded cystine bridges.

In particular aspects, the chaotropic auxiliary comprises guanidine or guanidine hydrochloride. In particular aspects, the chaotropic auxiliary comprises urea.

In particular embodiments the amine base may comprise arginine, tris, or the like. In particular aspects, the amine base is ethanolamine. In particular aspects, the diluent solution comprises about 10 mM of the amine base.

In particular aspects, the refold diluent solution comprises cystamine at a predetermined concentration to provide a refold solution that comprises cystamine at about 0.2 to 0.5 mole cystamine per mole of thiol in the precursor molecule.

In particular aspects, the refold diluent solution comprises cystamine at a predetermined concentration to provide a refold solution that comprises a DTT/cystamine redox ratio between 5:1 to 9:1.

In particular aspects, the refold diluent solution comprises cystamine at a predetermined concentration to provide a refold solution that comprises a DTT/cystamine redox ratio of about 6.5:1 for the refold solution.

In particular aspects, the refold diluent solution comprises cystamine at a predetermined concentration to provide a refold solution that comprises about 345 to 404 µM cystamine.

In particular aspects, the refold diluent solution comprises cystamine at a predetermined concentration to provide a refold solution that comprises about 345 µM cystamine.

In particular aspects, step (c) comprises incubating the refold solution for about 5 to 10 hours and at a temperature of about 9° to 11° C.

In particular aspects, step (e) comprises reacting the precursor insulin or insulin analog having correctly bonded cysteine bridges from step (d) with citraconic anhydride to produce a citraconylated precursor insulin or insulin analog having correctly bonded cysteine bridges and then reacting the citraconylated precursor insulin or insulin analog having correctly bonded cysteine bridges with trypsin or a trypsin-like enzyme and optionally additionally with the carboxypeptidase B or mixture of the enzymes to provide a citraconylated insulin or insulin analog having correctly bonded cysteine bridges.

In particular aspects, step (f) comprises reacting the citraconylated insulin or insulin analog having correctly bonded cysteine bridges with acetic acid and then purifying the insulin or insulin analog having correctly bonded cysteine bridges to provide insulin or insulin analog having correctly bonded cysteine bridges The present invention further provides a process for obtaining an insulin or insulin analog having correctly bonded cysteine bridges, which comprises (a) solubilizing a suspension of inclusion bodies obtained from a microbiological host comprising a precursor of insulin or insulin analog having incorrectly bonded cysteine bridges in an aqueous solution comprising a chaotropic auxiliary, dithiothreitol (DTT), and an amine base to provide a solubilization solution comprising about 3.8 to 4.3 M of a chaotropic auxiliary, about 2.2 to 2.8 mM DTT, about 0.3 to 0.4 M of an amine base, about 12 to 18 g/L of the precursor of insulin or insulin analog having incorrectly bonded cysteine bridges, and at a pH of about 10.2 to 11.0; (b) diluting the solubilization solution about 10-fold with a refold diluent solution comprising the amine base and cystamine to the diluted solubilization solution to provide a refold solution; (c) incubating the refold solution for a time and temperature sufficient to provide a refold solution. comprising the precursor of insulin or insulin analog having correctly bonded cysteine bridges; (d) reducing the pH of the refold solution from step (c); (e) isolating the precursor of insulin or insulin analog having correctly bonded cystine bridges by anion exchange chromatography; (f) cleaving the precursor of insulin or insulin analog having correctly bonded cystine bridges from step (e) with trypsin or a trypsin-like enzyme and optionally additionally with carboxypeptidase B or mixture of the enzymes to provide the insulin or insulin analog having correctly bonded cystine bridges; and (g) purifying the insulin or insulin analog having correctly bonded cystine bridges.

In particular aspects, the chaotropic auxiliary comprises guanidine or guanidine hydrochloride. In particular aspects, the chaotropic auxiliary comprises urea.

In particular embodiments the amine base may comprise arginine, tris, or the like. In particular aspects, the amine base is ethanolamine. In particular aspects, the diluent solution comprises about 10 mM of the amine base.

In particular aspects, step (b) comprises cystamine at a predetermined concentration to provide a refold solution that comprises cystamine at about 0.2 to 0.5 mole cystamine per mole of thiol in the precursor molecule.

In particular aspects, the refold diluent solution comprises cystamine at a predetermined concentration to provide a refold solution that comprises a DTT/cystamine redox ratio between 5:1 to 9:1.

In particular aspects, the refold diluent solution comprises cystamine at a predetermined concentration to provide a refold solution that comprises a DTT/cystamine redox ratio of about 6.5:1 for the refold solution.

In particular aspects, the refold diluent solution comprises cystamine at a predetermined concentration to provide a refold solution that comprises about 345 to 404 µM cystamine.

In particular aspects, the refold diluent solution comprises adding cystamine at a predetermined concentration to the diluted solubilization solution to provide a refold solution that comprises about 345 µM cystamine.

In particular aspects, step (c) comprises incubating the refold solution for about 5 to 10 hours and at a temperature of about 9° to 11° C.

In particular aspects, step (f) comprises reacting the precursor insulin or insulin analog having correctly bonded cysteine bridges from step (e) with citraconic anhydride to produce a citraconylated precursor insulin or insulin analog having correctly bonded cysteine bridges and then reacting the citraconylated precursor insulin or insulin analog having correctly bonded cysteine bridges with trypsin or a trypsin-like enzyme and optionally additionally with the carboxypeptidase B or mixture of the enzymes to provide a citraconylated insulin or insulin analog having correctly bonded cysteine bridges.

In particular aspects, step (g) comprises reacting the citraconylated insulin or insulin analog having correctly bonded cysteine bridges with acetic acid and then purifying the insulin or insulin analog having correctly bonded cysteine bridges to provide insulin or insulin analog having correctly bonded cysteine bridges.

Definitions

Insulin—as used herein, the term means the active principle of the pancreas that affects the metabolism of carbohydrates in the animal body and which is of value in the treatment of diabetes mellitus. The term includes synthetic and biotechnologically derived products that are the same as, or similar to, naturally occurring insulins in structure, use, and intended effect and are of value in the treatment of diabetes mellitus. The term is a generic term that designates the 51 amino acid heterodimer comprising the A-chain peptide having the amino acid sequence is GIVEQCCTSIC-SLYQLENYCN (SEQ ID NO: 1) and the B-chain peptide having the amino acid sequence is FVNQHLCG-SHLVEALYLVCGERG FFYTPKT (SEQ ID NO: 2), wherein the insulin has the following cystine bridges: cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond.

Insulin analog or analogue—the term as used herein includes any heterodimer analogue or single-chain analogue that comprises one or more modification(s) of the native A-chain peptide and/or B-chain peptide. Modifications include but are not limited to substituting an amino acid for the native amino acid at a position selected from A4, A5, A8, A9, A10, A12, A13, A14, A15, A16, A17, A18, A19, A21, B1, B2, B3, B4, B5, B9, B10, B13, B14, B15, B16, B17, B18, B20, B21, B22, B23, B26, B27, B28, B29, and B30; deleting any or all of positions B1-4 and B26-30; or conjugating directly or by a polymeric or non-polymeric linker one or more acyl, polyethylene glycol (PEG), or saccharide moiety (moieties); or any combination thereof. As exemplified by the N-linked glycosylated insulin analogues disclosed herein, the term further includes any insulin heterodimer and single-chain analogue that has been modified to have at least one N-linked glycosylation site and in particular, embodiments in which the N-linked glycosylation site is linked to or occupied by an N-glycan. Examples of insulin analogues include but are not limited to the heterodimer and single-chain analogues disclosed in published international application WO20100080606, WO2009/099763, and WO2010080609, the disclosures of which are incorporated herein by reference. Examples of single-chain insulin analogues also include but are not limited to those disclosed in published International Applications WO9634882, WO95516708, WO2005054291, WO2006097521, WO2007104734, WO2007104736, WO2007104737, WO2007104738, WO2007096332, WO2009132129; U.S. Pat. Nos. 5,304,473 and 6,630,348; and Kristensen et al., Biochem. J. 305: 981-986 (1995), the disclosures of which are each incorporated herein by reference.

The term further includes single-chain and heterodimer polypeptide molecules that have little or no detectable activity at the insulin receptor but which have been modified to include one or more amino acid modifications or substitutions to have an activity at the insulin receptor that has at least 1%, 10%, 50%, 75%, or 90% of the activity at the insulin receptor as compared to native insulin and which further includes at least one N-linked glycosylation site. In particular aspects, the insulin analogue is a partial agonist that has less than 80% (or 70%) activity at the insulin receptor as does native insulin. These insulin analogues, which have reduced activity at the insulin growth hormone receptor and enhanced activity at the insulin receptor, include both heterodimers and single-chain analogues.

Single-chain insulin or single-chain insulin analog—as used herein, the term encompasses a group of structurally-related proteins wherein the A-chain peptide or functional analogue and the B-chain peptide or functional analogue are covalently linked by a peptide or polypeptide of 2 to 35 amino acids or non-peptide polymeric or non-polymeric linker and which has at least 1%, 10%, 50%, 75%, or 90% of the activity of insulin at the insulin receptor as compared to native insulin. The single-chain insulin or insulin analogue further includes three disulfide bonds: the first disulfide bond is between the cysteine residues at positions 6 and 11 of the A-chain or functional analogue thereof, the second disulfide bond is between the cysteine residues at position 7 of the A-chain or functional analogue thereof and position 7 of the B-chain or functional analogue thereof, and the third disulfide bond is between the cysteine residues at position 20 of the A-chain or functional analogue thereof and position 19 of the B-chain or functional analogue thereof.

Connecting peptide or C-peptide—as used herein, the term refers to the connection moiety "C" of the B-C-A polypeptide sequence of a single chain preproinsulin-like molecule. Specifically, in the natural insulin chain, the C-peptide connects the amino acid at position 30 of the B-chain and the amino acid at position 1 of the A-chain. The term can refer to both the native insulin C-peptide, the monkey C-peptide, and any other peptide from 3 to 35 amino acids that connects the B-chain to the A-chain thus is meant to encompass any peptide linking the B-chain peptide to the A-chain peptide in a single-chain insulin analogue (See for example, U.S. Published application Nos. 20090170750 and 20080057004 and WO9634882) and in insulin precursor molecules such as disclosed in WO9516708 and U.S. Pat. No. 7,105,314.

Proinsulin—as used herein, the term refers to a molecule consisting of a B-chain peptide, which is fused to the N-terminus of a C-peptide which in turn is fused at its C-terminus to the N-terminus of an A-chain peptide.

Precursor insulin—as used herein, the term refers to a fusion protein comprising a leader peptide fused to the N-terminus of a proinsulin. The precursor insulin analog may optionally include one or more extension or spacer peptides between the C-terminus of the leader peptide and the N-terminus of the B-chain peptide.

Proinsulin analog—as used herein, the term refers to a molecule consisting of a B-chain peptide or B-chain peptide analog, which is fused to the N-terminus of a C-peptide which in turn is fused at its C-terminus to the N-terminus of an A-chain peptide or A-chain peptide analog, with the proviso that at least one of the A-chain peptide or B-chain peptide includes a substitution, deletion, or other modification not present in the native peptide.

Precursor insulin analog—as used herein, the term refers to a fusion protein comprising a leader peptide fused to the N-terminus of a proinsulin analog.

Precursor protein—as used herein, the term refers either to a precursor insulin or a precursor insulin analog.

Amino acid modification—as used herein, the term refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

Cystamine—as used herein, has the structure

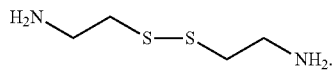

Cystamine is commonly available as cystamine dihydrochloride (diHCl).

Cysteamine is the reduced form of cystamine and has the structure

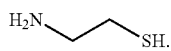

DETAILED DESCRIPTION OF THE INVENTION

Figure 1:
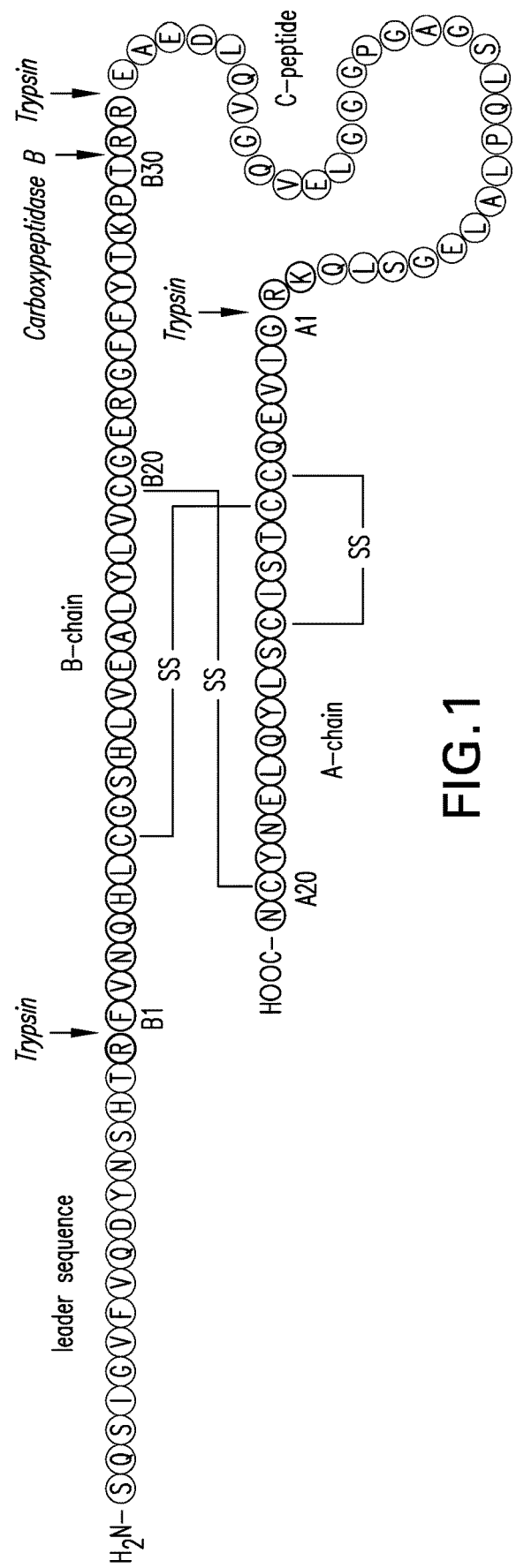
FIG. 1 shows the amino acid sequence of precursor insulin lispro (SEQ ID NO:4). The trypsin and carboxypeptidase B cleavage sites are shown.

Processes for production of insulin or insulin analogs from its precursor protein isolated post-fermentation in the form of insoluble inclusion bodies in which the precursor protein is incorrectly folded (incorrectly bonded cystine bridges) generally include several steps. First, the precursor protein contained in the inclusion bodies must be solubilized and denatured (i.e., disulfide linkages reduced). The solubilized, reduced precursor protein must then be refolded to produce the native insulin disulfide linkages, and finally the correctly folded precursor protein must be processed enzymatically to produce the correctly folded insulin or insulin analog, has correctly bonded cystine bridges.

Since the precursor protein contained in the inclusion bodies is incorrectly folded with improperly formed cystine disulfide bridges, and is also highly aggregated, a method is required for complete or at least partial solubilization of the precursor protein and reduction of the incorrectly formed disulfide linkages. Methods that are simple, rapid, and complete, and which yield high concentrations (greater than 10 g/L to minimize process volume in the subsequent refolding) are desired.

For solubilizing and refolding the precursor proteins, procedures previously reported have generally employed solutions of a chaotropic auxiliary (e.g., urea or guanidine), cysteine as the thiol reducing agent, and various buffers to achieve a pH of about 10.5 for solubilization and reduction. Various premixing and/or heating schemes, and the use of the reductant in amounts at or exceeding 1 mole cysteine per mole protein thiol in the precursor protein have been employed for best results. We have now found that rapid and complete solubilization at high concentrations of the precursor protein can be achieved in aqueous solutions containing a chaotropic auxiliary, a strongly basic amine, and small amounts of DTT as the thiol reducing agent. This method is advantageous over previous methods in that it is simple, requiring little more than mixing the reagents with the inclusion bodies and stirring briefly to achieve complete dissolution. The amount of DTT employed is about 0.2 mole of per mole of thiol in the insulin or insulin analog precursor molecule protein thiol. This corresponds to about 0.4 mole of reductant thiol per mole of insulin or insulin analog precursor molecule protein thiol content, and is well below the ratios previously utilized with cysteine as reductant. Importantly, the need for only very low levels of DTT to achieve complete solubilization and reduction at this stage enables the use of a new, highly efficient refolding procedure, as discussed below.

In addition to solubilization and reduction, processes for production of insulin or insulin analogs from precursor proteins require methods for correctly refolding the insulin or insulin analog precursor protein. Methods that afford high yields are clearly preferred, since this reduces the burden on upstream fermentation processes with respect to precursor production, and on downstream purification processes for byproduct removal. Precursor protein concentration during refolding is also a major consideration. For refolding at concentrations significantly below about 1 g/L, process volumes become problematic at large scale. For refolding of proteins in general, formation of byproducts such as aggregates is concentration dependent, and yields tend to decline at higher concentrations. Refolding time is also an issue. Clearly, refolding procedures that are completed within a few hours are preferred over those requiring much longer times.

For refolding precursor proteins, the procedures previously reported generally employ dilution to reduce the concentrations of denaturants (typically urea or guanidine) and redox reagents (particularly cysteine and in some cases with addition of cystine) in the solubilization mixtures at high pH to concentrations that favor formation of the native proinsulin structure. Moderate yields have been obtained at concentrations at or above 1 g/L. Using the low level DTT solubilization and reduction procedure described above, we have now found that refolding of insulin or insulin analog precursor proteins can readily be accomplished in high yield by dilution the solubilization and reduction mixture with aqueous solutions containing a strongly basic amine at high pH and small amounts of cystamine. Refolding proceeds to some degree simply by diluting the solubilization and reduction mixture to a concentration of the urea denaturant below about 2 M. Much higher yields may be obtained at lower urea concentrations. DTT, used as the reductant during solubilization, is a very strong thiol reducing agent, but a poor catalyst for protein disulfide formation and exchange.

In the absence of added cystamine, refolding is sluggish. However, as shown by the present process, improved refolding may be obtained when cystamine is present in the refold solution at about 0.2 to 0.5 mole per mole of protein thiol contained in the insulin or insulin analog precursor molecule, and the urea is diluted to below about 0.7 M. Under these conditions, the cystamine is converted to a cystamine/cysteamine redox couple which allows for rapid formation and equilibration of protein disulfide linkages. In particular embodiments, the cystamine is added at a predetermined concentration to provide a refold solution comprising a DTT/cystamine redox ratio of about 5:1 to about 9:1, or about 5.4:1 to about 8.1:1, or about 6.5:1. The native configuration of insulin or insulin analog precursor protein is strongly favored thermodynamically at high pH and low urea concentrations, and yields of 70 to 90% are achieved at precursor protein concentrations of up to 2 g/L. Higher concentrations of cystamine are not required, since mixed disulfide formation with the protein reduces yield. In addition, the low levels of redox reagents employed in the process as disclosed herein allow for sufficient aeration to be obtained with gentle agitation to drive the cystamine/cysteamine redox couple to favor complete protein disulfide formation as refolding proceeds. This avoids the presence of significant amounts of partially reduced forms of the precursor protein in the mixture post refolding, which is typically complete within 6 to 12 hours.

Processes for production of insulin and insulin analogs which utilize enzymatic cleavage of precursor protein are known (e.g. U.S. Published Application No. 2012/0214965, which is incorporated herein as reference in its entirety). It would be readily apparent to one skilled in the art how these could be applied perhaps with minor modifications to the correctly folded precursor protein obtained using the solubilization and refolding process of the present invention to produce insulin and insulin analogs. In addition, the second part of this invention relates to the purification of precursor protein by anion exchange chromatography, and its subsequent conversion to insulin.

For the manufacture of insulin or insulin analog, a precursor protein comprising a leader peptide fused to the N-terminus of a proinsulin or proinsulin analog (precursor protein) is expressed in a genetically modified *E. coli* host. The precursor protein is initially isolated post fermentation in the form of insoluble inclusion bodies (IBs) made up of incorrectly folded precursor protein in association with host cell macro-molecules. One aspect of the current invention relates to a process for solubilization and refolding of the precursor protein to obtain the correctly folded precursor protein in very high yield.

Solubilization:

For solubilization, the incorrectly folded, insoluble, precursor protein contained in a suspension of inclusion bodies (IBs) is first solubilized at high pH in an aqueous solution containing a chaotropic auxiliary (e.g., urea, guanidine, or guanidine hydrochloride), a thiol thiol reducing agent (e.g., dithiothreitol (DTT)), and a strongly basic amine (e.g., ethanolamine base) for pH control. Final concentrations of the precursor protein, chaotropic auxiliary, DTT, and the amine base are during solubilization optimized to achieve (i) complete solubilization, (ii) pH control, and (iii) reasonable dilution requirements for induction of refolding. In a particular embodiment, the process utilizes about 3.8 to 4.3 M urea, about 2.2 to 2.8 mM DTT, a target concentration for the precursor protein of about 12 to 18 g/L, and about 265 to 365 mM amine base to achieve a pH of about 10.5. Ethanolamine and arginine have been used successfully as the amine base component, which must be strongly basic to achieve the optimum pH (about 10.5) needed for solubilization and refolding. Ethanolamine afforded high yields, and none of the protein carbamylation commonly seen when urea is utilized as a chaotrope has been observed.

Refolding:

For refolding, the solubilization solution is diluted at 10° C. with a diluent solution containing the amine base, cystamine (a disulfide oxidant) and, optionally, hexylene glycol (a co-solvent) to provide a refold solution having concentrations of urea, the precursor protein, thiol/disulfide redox components, and a pH which favors refolding. In an embodiment of the process, the refold solution comprises about 0.38 to 0.43 M urea, about 1.2 to 1.8 g/L precursor protein, about 0.345 to 0.404 mM cystamine, about 0.22 to 2.8 mM DTT, and about 40 mM ethanolamine, and has a pH at about 10.5. After dilution, the refold solution is stirred to maintain aeration. As refolding proceeds, air oxidation is used to drive the disulfide formation to completion. The progress of the refolding may be monitored using reverse phase HPLC.

The pH of the refold solution is adjusted to about 9.0 to 9.4 or about 9.2 to provide a clarified post-refold solution, which is then clarified by filtration or centrifugation prior to produce a solution that may be applied to anion exchange (AEX) chromatography (described below).

In an alternative embodiment, the pH of the refold solution is adjusted to about 3.7 to precipitate host cell related impurities leaving the correctly folded precursor protein in a second post-refold solution. The second post-refold solution is then filtered or centrifuged to remove the precipitated material to produce a clarified second post-refold solution that may be reacted with trypsin or trypsin-like enzyme and optionally additionally with carboxypeptidase B or mixture of the enzymes to provide an insulin or insulin analog having correctly bonded cystine bridges.

Generally, in either embodiment, yields may be reduced as the concentration of the precursor protein is increased. Lower recoveries of correctly folded precursor protein may be obtained at chaotropic auxiliary concentrations above about 0.7 M. Low temperature (10° C.) may improve the yield, primarily at higher protein concentrations. The presence of the hexylene glycol co-solvent, added at 10% by volume, has little effect on the composition of the refold solution at the end of refolding, but improves recovery post acidification, particularly if low pH is used to precipitate host cell related impurities.

AEX Purification:

Anion exchange (AEX) chromatography may be used to concentrate and purify the correctly folded precursor protein, as well as for buffer exchange, prior to reacting with trypsin or trypsin-like enzyme and optionally additionally with carboxypeptidase B or mixture of the enzymes to provide an insulin or insulin analog having correctly bonded cystine bridges. The pH of the clarified post-refold solution is adjusted to about 9.4 with sodium hydroxide and it is diluted with water, if necessary, to achieve a conductivity of less than 2.5 mS/cm. The resulting solution is loaded onto a column packed with an anion exchange resin, e.g., DEAE Sepharose Fast Flow, which has been equilibrated with an equilibration solution comprising about 50 mM sodium borate and 2.5 mM sodium chloride at about pH 9.4. Other similar resins may also be used with some modification of chromatographic parameters. Flow rates during the loading and subsequent elution steps are adjusted to maintain a residence time of about five to seven minutes, and a loading factor of about 23 g of the correctly folded precursor protein per L of column resin may be used. After loading, the column is washed with about five column volumes (CV) of equilibration solution (50 mM sodium borate, 2.5 mM sodium chloride at pH 9.4), and then with about six CV of elution solution (about 50 mM sodium borate and 160 mM sodium chloride at pH 9.0). During elution, the ultraviolet (UV) absorbance of the eluent at 280 nm is monitored. The main peak observed during elution with the 160 mM sodium chloride elution solution is collected to provide a post-AEX pool that contains the correctly folded insulin precursor. Post-AEX purification or isolation, the concentration of correctly folded precursor protein is determined by reverse phase high pressure liquid chromatography (RP-HPLC).

Enzymatic Digestion:

The correctly folded precursor protein is enzymatically converted to correctly folded insulin or insulin analog using trypsin or trypsin-like enzyme and optionally additionally carboxypeptidase B or a mixture of the enzymes. The choice of whether to use carboxypeptidase B will depend on the precursor protein. For example, a correctly folded precursor protein comprising the amino acid sequences for insulin lispro or native human insulin may be reacted with trypsin and carboxy peptidase B to produce correctly folded insulin lispro or native human insulin. As shown in FIG. 1, trypsin will cleave the correctly folded precursor protein containing the amino acid sequences for insulin lispro at the positions shown and the carboxypeptidase B will cleave as shown to produce correctly folded insulin lispro. Trypsin from a variety of sources may be utilized for this purpose. Bovine or porcine trypsin derived from animal sources may be used, but for pharmaceutical purposes, recombinant trypsin containing human, bovine, or porcine sequences may be used. Carboxypeptidase B from a variety of sources may be utilized for this purpose. Bovine, rat, or porcine carboxypeptidase B derived from animal sources may be used, but for pharmaceutical purposes, recombinant carboxypeptidase containing human, bovine, rat, or porcine sequences may be used.

In a typical procedure, an aqueous solution of trypsin is added to the clarified second post-refold solution or post-AEX pool to provide a digestion solution that is stirred at about 21° C. In particular embodiments, the concentration of precursor protein in the post-refold or post-AEX pool is adjusted to about 6 g/L and the pH adjusted to about 8.5 with HCl or NaOH. In particular embodiments, the trypsin is added at a ratio (w/w) of about 1:12,100 or 1:11,000, enzyme to precursor protein or about 480:1 to about 520:1 or about 500:1 of USP enzyme to gram of precursor protein. In particular aspects, carboxypeptidase B (e.g., rat carboxypeptidase B) is added at a ratio of about 20 USP carboxypeptidase B to gram of precursor protein of about 18:1 to about 22:1 or about 20:1. The digestion solution is allowed to stand at this temperature for about 12 hours to complete the digestion. Some adjustment of the enzyme to correctly folded precursor protein ratio is required when trypsin from other sources are utilized. The progress of the digest may be monitored by reverse phase HPLC. For this purpose, aliquots at various time points in the digestion can be acidified to pH 8.0 to 2.4 with HCl to stop the digest. The rate of digestion increases with increasing enzyme to correctly folded precursor protein ratio and also with temperature. However, both incomplete digestion and over digestion reduce yield and complicate the subsequent purification. When enzyme to correctly folded precursor protein ratios are used at which the reaction is complete within about eight to 16 hours, high yields are achieved without the need for intensive real time analytical monitoring.

In particular embodiments, the precursor protein in the clarified second post-refold solution or the AEX pool may be citraconylated with citraconic anhydride as described below prior to the enzymatic digest to reduce the occurrence of unwanted enzyme digestion byproducts.

Figure 2:
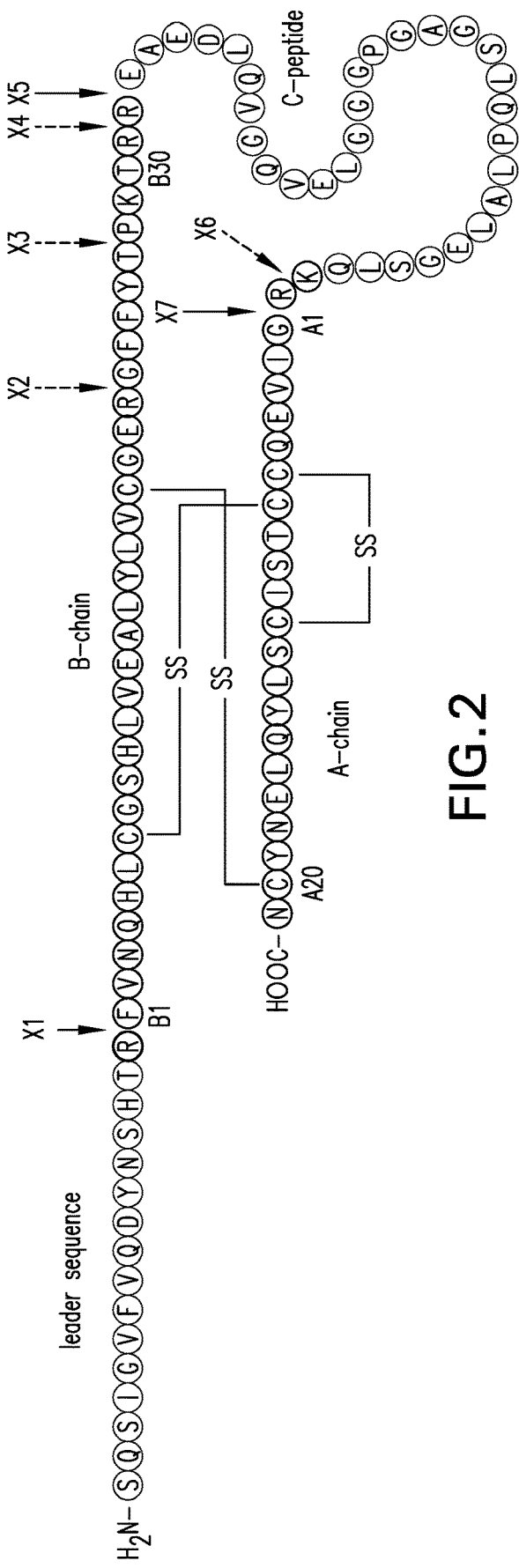
FIG. 2 shows the amino acid sequence of precursor insulin glargine (SEQ ID NO:3). Trypsin cleavage sites are shown by X1, X5, and X7. Potential, less active trypsin cleavage sites are shown by X2, X3, X4, and X6.

Citraconylation:

Trypsin catalyzes the cleavage of protein amide bonds on the C-terminal side of arginine and lysine residues, and is used in this process for conversion of the correctly folded precursor protein to correctly folded insulin or insulin analog. However, the amino acid sequence of the correctly folded precursor protein contains in addition to the primary trypsin cleavage sites X1, X5, and X7, several less reactive trypsin cleavage sites (X2, X3, X4, and X6). Cleavage at these less reactive sites results in unwanted digestion byproducts. For example, FIG. 2 shows a correctly folded precursor molecule containing the amino acid sequences for insulin glargine. The process for producing correctly folded insulin glargine requires trypsin cleavage to occur at sites X1, X5 and X7. Reaction byproducts occur when trypsin cleaves at alternate less reactive sites in the correctly folded precursor protein (e.g., at positions X2, X3, X4, and/or X6) or missed cleavage at X1, X5, and/or X7. To improve the yield of correctly folded insulin or insulin analog, citraconic anhydride may be used to acylate the lysine ε-amino groups and the N-terminal amine of the correctly folded precursor protein to produce protected, correctly folded precursor protein. Protein amide bonds containing resulting citraconylated lysine residues on the N-terminal side are not cleaved by trypsin, thus eliminating unproductive cleavages at sites X3 and X6.

For citraconylation, the post-AEX pool containing the correctly folded precursor protein is treated with citraconic anhydride (about 0.20 to 0.24 mL of neat liquid citraconic anhydride per gram of correctly folded precursor protein in the pool determined by reverse phase HPLC analysis) prior to the enzymatic digestion. The citraconic anhydride is added by continuous infusion over 30 minutes or total amount is divided into three bolus additions, which are added at 10 minute intervals. After the addition is complete, the pH is adjusted to about 8.3 to 8.7 if needed with HCl or NaOH and stirred for about 1.75 to about 2.25 hours to insure complete hydrolysis of excess reagent. The citraconyl protecting groups are stable under basic conditions, but are removed with acidification post digest. After citraconylation, enzymatic digestion may be performed as described above. After the digest is complete, acetic acid is added to a concentration of about 140 to 160 mM to stop the reaction, the pH is adjusted to about 2.2 to 2.4 with 5N HCl, and the solution is stirred for about four hours to complete deprotection and provide a correctly folded insulin or insulin analog.

The correctly folded insulin or insulin analog may be further purified using processes known in the art for producing purified insulin or insulin analog.

The following examples are intended to promote a further understanding of the present invention.

Example 1

This example illustrates the use of the process for refolding a precursor insulin glargine protein into its proper configuration. The precursor insulin glargine has the amino acid sequence SQSIGVFVQ DYNSHTR FVN QHLCG-SHLVE ALYLVCGERG FFYTPKTRREAEDLQVGQVE LGGGPGAGSL QPLALEGSLQ KRGIVEQCCT SICSLY-QLEN YCG (SEQ ID NO:3).

Inclusion body (IB) protein slurry comprising precursor insulin glargine at a concentration of about 30 g/L in water is provided. After charging the IBs into the water, ethanolamine is added as a neat liquid to a final concentration of about 315 mM followed by the addition of 8 M urea to a final concentration of about 4.0 M. Finally, a 1 M aqueous dithiothreitol (DTT) solution is added to target a concentration of about 2.5 mM, and the mixture is agitated for a minimum of 30 minutes to complete the IB solubilization.

The protein is diluted approximately 10-fold to a target precursor insulin glargine concentration of about 1.6 g/L. First, the target amount of refold diluent solution is prepared then the required amount of refold oxidizing agent (about 384 µM) is added and mixed until homogeneous. Next, the solubilized protein solution is transferred into the refold diluent solution with a minimal level of agitation needed to ensure solution mixing while maintaining a solution temperature of 10° C. (±2° C.). The refold reaction is agitated at 10° C. until the rate of conversion to correctly folded precursor insulin glargine falls below 5% per hour, as measured by the POROS HPLC assay, at which point the reaction is quenched. After completion of the refold, the reaction is stopped/slowed down by acidifying the refold solution, with 2N hydrochloric acid, to a pH of about 9.2 at 10° C. The temperature is maintained at 10° C. during pH adjustment.

Example 2

This example illustrates the use of the process for refolding a precursor insulin lispro protein into its proper configuration. The precursor insulin lispro has the amino acid sequence SQSIGVFVQ DYNSHTR FVN QHLCGSHLVE ALYLVCGERG FFYTKPTRREAEDLQVGQVE LGGGP-GAGSL QPLALEGSLQ KRGIVEQCCT SICSLYQLEN YCN (SEQ ID NO:4).

Inclusion body (IB) protein slurry comprising precursor insulin lispro at a concentration of about 30 g/L in water is provided. After charging the IBs into the water, ethanolamine is added as a neat liquid to a final concentration of about 315 mM followed by the addition of 8 M urea to a final concentration of about 4.0 M. Finally, a 1 M aqueous dithiothreitol (DTT) solution is added to target a concentration of about 2.5 mM, and the mixture is agitated for a minimum of 30 minutes to complete the IB solubilization.

The protein is diluted approximately 10-fold to a target precursor insulin lispro concentration of about 1.6 g/L. First, the target amount of refold diluent solution is prepared then the required amount of refold oxidizing agent (about 384 μM) is added and mixed until homogeneous. Next, the solubilized protein solution is transferred into the refold diluent solution with a minimal level of agitation needed to ensure solution mixing while maintaining a solution temperature of 10° C. (±2° C.). The refold reaction is agitated at 10° C. until the rate of conversion to correctly folded precursor insulin glargine falls below 5% per hour, as measured by the POROS HPLC assay, at which point the reaction is quenched. After completion of the refold, the reaction is stopped/slowed down by acidifying the refold solution, with 2N hydrochloric acid, to a pH of about 9.2 at 10° C. The temperature is maintained at 10° C. during pH adjustment.

Example 3

This example illustrates the use of the process for refolding a precursor insulin glargine protein into its proper configuration and digesting with trypsin to produce insulin glargine having an A-chain peptide having the amino acid sequence GIVEQCCT SICSLYQLEN YCG (SEQ ID NO:5) and a B-chain peptide having the amino acid sequence FVN QHLCGSHLVE ALYLVCGERG FFYTPKTRR (SEQ ID NO:6) bonded together by the six cysteine residues forming three disulfide bonds between following positions: A6-A11; A7-B7; and A20-B19.

Inclusion body (IB) protein slurry comprising precursor insulin glargine at a concentration of about 30 g/L in water is provided. After charging the IBs into the water, ethanolamine is added as a neat liquid to a final concentration of about 315 mM followed by the addition of 8 M urea to a final concentration of about 4.0 M. Finally, a 1 M aqueous dithiothreitol (DTT) solution is added to target a concentration of about 2.5 mM, and the mixture is agitated for a minimum of 30 minutes to complete the IB solubilization.

The protein is diluted approximately 10-fold to a target precursor insulin glargine concentration of about 1.6 g/L. First, the target amount of refold diluent solution is prepared then the required amount of refold oxidizing agent (about 384 μM) is added and mixed until homogeneous. Next, the solubilized protein solution is transferred into the refold diluent solution with a minimal level of agitation needed to ensure solution mixing while maintaining a solution temperature of 10° C. (±2° C.). The refold reaction is agitated at 10° C. until the rate of conversion to correctly folded precursor insulin glargine falls below 5% per hour, as measured by the POROS HPLC assay, at which point the reaction is quenched. After completion of the refold, the reaction is stopped/slowed down by acidifying the refold solution, with 2N hydrochloric acid, to a pH of about 9.2 at 10° C. to produce a post-refold solution. The temperature is maintained at 10° C. during pH adjustment.

Cellular debris and precipitated Host Cell Protein (HCP) is separated out prior to loading on the AEX column. In preparation for the clarification, the temperature of the post-refold solution is increased from 10° C. to 20° C. over a span of 60-120 minutes. The clarification is performed via two banks of depth filters and one bank of 0.22 μm membrane filters, all in series. Depth filters consist of CUNO EXT 60ZA05A filters (bank #1, 56 m² total area) in series with CUNO EXT 90ZA08A filters (bank #2, also 56 m2). Additionally in series with the depth filters are 0.22 μm filters (9 m2 total area). Both banks of depth filters are flushed together with 54 L/m² of water, or approximately 3000 L, prior to use. Once the depth filters have been flushed, the 0.22 μm filters are flushed (>20 L/m2) by flowing water through depth filter banks #1 and #2 and then through the 0.22 μm filters to drain due to equipment restrictions. An air-displacement of the flush water on the depth filters is performed before introducing product. The filters are operated at first under constant flux and then, as the filters start fouling, the flow rate is reduced to prevent the pressure from exceeding 40 psig. After the post refold solution has been completely processed, a recovery water chase is performed (25-30 L/m2) to maximize recovery of correctly folded precursor insulin glargine into a clarified post-refold solution.

The pH of the clarified post-refold solution is adjusted to about 9.4 with sodium hydroxide and it is diluted with water, if necessary, to achieve a conductivity of less than 2.5 mS/cm. The resulting solution is loaded onto a column packed with DEAE Sepharose Fast Flow, which has been equilibrated with an equilibration solution comprising about 50 mM sodium borate and 2.5 mM sodium chloride at pH 9.4. Flow rates during the loading and subsequent elution steps are adjusted to maintain a residence time of about five to seven minutes, and a loading factor of about 23 g of the correctly folded precursor insulin glargine per L of column resin is used. After loading, the column is washed with about five column volumes (CV) of equilibration solution (50 mM sodium borate, 2.5 mM sodium chloride at pH 9.4), and then with about six CV of elution solution (about 50 mM sodium borate and 160 mM sodium chloride at pH 9.0). The main peak observed during elution with the 160 mM sodium chloride elution solution is collected to provide a post-AEX pool that contains the correctly folded insulin precursor insulin glargine.

Prior to beginning the protection reaction, the concentration of correctly folded insulin precursor insulin glargine in the post-AEX pool is determined. Next, three bolus shots of neat citraconic anhydride are added to the AEX pool at room temperature to achieve the correct ratio of anhydride to correctly folded insulin precursor insulin glargine. After the anhydride addition is complete, the pH is adjusted to 8.5 (if needed) with HCl or NaOH solution and the protection reaction is allowed to proceed for 2±0.25 hours.

After the protection reaction is complete, the pH is checked and, if it has changed, titrated back to 8.5 using an HCl or NaOH solution. The trypsin solution is then added to achieve a ratio of trypsin to correctly folded insulin precursor insulin glargine of about 1:11,000 by mass. Digestion proceeds for 12±1 hours. After digestion is complete, the reaction is stopped by first adding acetic acid to achieve a pool concentration of 150 mM acetate, and then adjusting the pH of the reaction pool to pH 2.4 using HCl. The deprotection reaction (in a volume of approximately 4100 L) then continues for 4±0.25 hours to produce correctly folded insulin glargine.

Example 4

This example illustrates the use of the process for refolding a precursor insulin lispro protein into its proper configuration and digesting with trypsin to produce insulin lispro having an A-chain peptide having the amino acid sequence GIVEQCCT SICSLYQLEN YCN (SEQ ID NO:1) and a B-chain peptide having the amino acid sequence FVN QHLCGSHLVE ALYLVCGERG FFYTKPT (SEQ ID NO:5) bonded together by the six cysteine residues forming three disulfide bonds between following positions: A6-A11; A7-B7; and A20-B19.

Inclusion body (IB) protein slurry comprising precursor insulin lispro at a concentration of about 30 g/L in water is provided. After charging the IBs into the water, ethanolamine is added as a neat liquid to a final concentration of about 315 mM followed by the addition of 8 M urea to a final concentration of about 4.0 M. Finally, a 1 M aqueous dithiothreitol (DTT) solution is added to target a concentration of about 2.5 mM, and the mixture is agitated for a minimum of 30 minutes to complete the IB solubilization.

The protein is diluted approximately 10-fold to a target precursor insulin lispro concentration of about 1.6 g/L. First, the target amount of refold diluent solution is prepared then the required amount of refold oxidizing agent (about 384 μM) is added and mixed until homogeneous. Next, the solubilized protein solution is transferred into the refold diluent solution with a minimal level of agitation needed to ensure solution mixing while maintaining a solution temperature of 10° C. (±2° C.). The refold reaction is agitated at 10° C. until the rate of conversion to correctly folded precursor insulin lispro falls below 5% per hour, as measured by the POROS HPLC assay, at which point the reaction is quenched. After completion of the refold, the reaction is stopped/slowed down by acidifying the refold solution, with 2N hydrochloric acid, to a pH of about 9.2 at 10° C. to produce a post-refold solution. The temperature is maintained at 10° C. during pH adjustment.

Cellular debris and precipitated Host Cell Protein (HCP) is separated out prior to loading on the AEX column. In preparation for the clarification, the temperature of the post-refold solution is increased from 10° C. to 20° C. over a span of 60-120 minutes. The clarification is performed via two banks of depth filters and one bank of 0.22 μm membrane filters, all in series. Depth filters consist of CUNO EXT 60ZA05A filters (bank #1, 56 m² total area) in series with CUNO EXT 90ZA08A filters (bank #2, also 56 m2). Additionally in series with the depth filters are 0.22 μm filters (9 m2 total area). Both banks of depth filters are flushed together with 54 L/m² of water, or approximately 3000 L, prior to use. Once the depth filters have been flushed, the 0.22 μm filters are flushed (>20 L/m2) by flowing water through depth filter banks #1 and #2 and then through the 0.22 μm filters to drain due to equipment restrictions. An air-displacement of the flush water on the depth filters is performed before introducing product. The filters are operated at first under constant flux and then, as the filters start fouling, the flow rate is reduced to prevent the pressure from exceeding 40 psig. After the post refold solution has been completely processed, a recovery water chase is performed (25-30 L/m2) to maximize recovery of correctly folded precursor insulin lispro into a clarified post-refold solution.

The pH of the clarified post-refold solution is adjusted to about 9.4 with sodium hydroxide and it is diluted with water, if necessary, to achieve a conductivity of less than 2.5 mS/cm. The resulting solution is loaded onto a column packed with DEAE Sepharose Fast Flow, which has been equilibrated with an equilibration solution comprising about 50 mM sodium borate and 2.5 mM sodium chloride at pH 9.4. Flow rates during the loading and subsequent elution steps are adjusted to maintain a residence time of about five to seven minutes, and a loading factor of about 23 g of the correctly folded precursor insulin lispro per L of column resin is used. After loading, the column is washed with about five column volumes (CV) of equilibration solution (50 mM sodium borate, 2.5 mM sodium chloride at pH 9.4), and then with about six CV of elution solution (about 50 mM sodium borate and 160 mM sodium chloride at pH 9.0). The main peak observed during elution with the 160 mM sodium chloride elution solution is collected to provide a post-AEX pool that contains the correctly folded insulin precursor insulin lispro.

Prior to beginning the enzymatic digest, the concentration of correctly folded precursor lispro in the post-AEX pool is determined and the product is diluted with water to 6 g/L. The pH is adjusted to 8.5 with HCl or NaOH solution (if needed). The trypsin solution is then added to achieve a ratio of trypsin to correctly folded insulin precursor insulin lispro of about 500:1 by Activity Units) and carboxypeptidase B is added at a ratio of 20:1 by Activity Units. Digestion proceeds for 16±1 hours. The enzymatic digest is agitated during enzyme addition. After digestion is complete, the pH is adjusted to pH 8.0 at 20° C. to provide correctly folded insulin lispro.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A process for obtaining a precursor molecule of insulin or insulin analog having correctly bonded cysteine bridges, which comprises:
   (a) providing a suspension of inclusion bodies obtained from *E. coli* host cells, wherein the inclusion bodies comprise precursor molecules of insulin or insulin analog having incorrectly bonded cysteine bridges;
   (b) solubilizing the inclusion bodies by adding urea, dithiothreitol (DTT), and ethanolamine to the suspension to provide a solubilization solution, wherein the solubilization solution comprises about 12 to 18 g/L of the precursor molecules of insulin or insulin analog having incorrectly bonded cysteine bridges, about 3.8 to 4.3 M urea, about 2.2 to 2.8 mM DTT, and about 265 to 365 mM ethanolamine, and has a pH of about 10.2 to 11.0;
   (c) diluting the solubilization solution about 10-fold with a refold diluent solution comprising ethanolamine and cystamine to provide a refold solution having about 1.2 to 1.8 g/L of the precursor molecules of insulin or insulin analog having incorrectly bonded cysteine bridges, 0.38 to 0.43 M urea, 345 to 404 µM cystamine, about 0.22 to 0.28 mM DTT, and about 26.5 to 36.5 mM ethanolamine and has a pH of about 10.2 to 11.0; and
   (d) incubating the refold solution with stirring to provide aeration for 6 to 12 hours to provide the precursor of insulin or insulin analog having correctly bonded cysteine bridges.

2. A process for obtaining an insulin or insulin analog having correctly bonded cysteine bridges, which comprises:
   (a) providing a suspension of inclusion bodies obtained from *E. coli* host cells microbiological host comprising a precursor of insulin or insulin analog having incorrectly bonded cysteine bridges in an aqueous solution comprising urea, dithiothreitol (DTT), and ethanolamine to provide a solubilization solution, wherein the solubilization solution comprises about 12 to 18 g/L of the precursor molecules of insulin or insulin analog having incorrectly bonded cysteine bridges, about 3.8 to 4.3 M urea, about 2.2 to 2.8 mM DTT, and about 265 to 365 mM ethanolamine, and has a pH of about 10.2 to 11.0;
   (b) diluting the solubilization solution about 10-fold with a refold diluent solution comprising ethanolamine and cystamine to provide a refold solution having about 1.2 to 1.8 g/L of the precursor molecules of insulin or insulin analog having incorrectly bonded cysteine bridges, 0.38 to 0.43 M urea, 345 to 404 µM cystamine, about 0.22 to 0.28 mM DTT, and about 26.5 to 36.5 mM ethanolamine and has a pH of about 10.2 to 11.0;
   (c) incubating the refold solution with stirring to provide aeration for 6 to 12 hours to provide a refold solution comprising a precursor of insulin or insulin analog having correctly bonded cysteine bridges;
   (d) reducing the pH of the refold solution from step (c) to about 9.0 to 9.4;
   (e) reacting the precursor of insulin or insulin analog having correctly bonded cysteine bridges from step (d) with trypsin or a trypsin-like enzyme and optionally additionally with carboxypeptidase B or mixture of the enzymes to provide the insulin or insulin analog having correctly bonded cysteine bridges; and (f) purifying the insulin or insulin analog having correctly bonded cysteine bridges to provide insulin or insulin analog having correctly bonded cysteine bridges.

3. The process of claim 2, wherein step (e) comprises reacting the precursor insulin or insulin analog having correctly bonded cysteine bridges from step (d) with citraconic anhydride to produce a citraconylated precursor insulin or insulin analog having correctly bonded cysteine bridges and then reacting the citraconylated precursor insulin or insulin analog having correctly bonded cysteine bridges with trypsin or a trypsin-like enzyme and optionally additionally with the carboxypeptidase B or mixture of the enzymes to provide a citraconylated insulin or insulin analog having correctly bonded cysteine bridges.

4. The process of claim 3, wherein step (f) comprises reacting the citraconylated insulin or insulin analog having correctly bonded cysteine bridges with acetic acid and then purifying the insulin or insulin analog having correctly bonded cysteine bridges to provide insulin or insulin analog having correctly bonded cysteine bridges.

5. A process for obtaining an insulin or insulin analog having correctly bonded cysteine bridges, which comprises:
(a) providing a suspension of inclusion bodies obtained from *E. coli* host cells microbiological host comprising a precursor of insulin or insulin analog having incorrectly bonded cysteine bridges in an aqueous solution comprising urea, dithiothreitol (DTT), and ethanolamine to provide a solubilization solution, wherein the solubilization solution comprises about 12 to 18 g/L of the precursor molecules of insulin or insulin analog having incorrectly bonded cysteine bridges, about 3.8 to 4.3 M urea, about 2.2 to 2.8 mM DTT, and about 265 to 365 mM ethanolamine, and has a pH of about 10.2 to 11.0;
(b) diluting the solubilization solution about 10-fold with a refold diluent solution comprising ethanolamine and cystamine to provide a refold solution having about 1.2 to 1.8 g/L of the precursor molecules of insulin or insulin analog having incorrectly bonded cysteine bridges, 0.38 to 0.43 M urea, 345 to 404 µM cystamine, about 0.22 to 0.28 mM DTT, and about 26.5 to 36.5 mM ethanolamine and has a pH of about 10.2 to 11.0;
(c) incubating the refold solution with stirring to provide aeration for 6 to 12 hours to provide a refold solution comprising a precursor of insulin or insulin analog having correctly bonded cysteine bridges;
(d) reducing the pH of the refold solution from step (c) to about 9.0 to 9.4;
(e) isolating the precursor of insulin or insulin analog having correctly bonded cysteine bridges by anion exchange chromatography;
(f) cleaving the precursor of insulin or insulin analog having correctly bonded cysteine bridges from step (e) with trypsin or a trypsin-like enzyme and optionally additionally with carboxypeptidase B or mixture of the enzymes to provide the insulin or insulin analog having correctly bonded cysteine bridges; and
(g) purifying the insulin or insulin analog having correctly bonded cysteine bridges.

6. The process of claim 5, wherein step (f) comprises reacting the precursor insulin or insulin analog having correctly bonded cysteine bridges from step (e) with citraconic anhydride to produce a citraconylated precursor insulin or insulin analog having correctly bonded cysteine bridges and then reacting the citraconylated precursor insulin or insulin analog having correctly bonded cysteine bridges with trypsin or a trypsin-like enzyme and optionally additionally with the carboxypeptidase B or mixture of the enzymes to provide a citraconylated insulin or insulin analog having correctly bonded cysteine bridges.

7. The process of claim 6, wherein step (g) comprises reacting the citraconylated insulin or insulin analog having correctly bonded cysteine bridges with acetic acid and then purifying the insulin or insulin analog having correctly bonded cysteine bridges to provide insulin or insulin analog having correctly bonded cysteine bridges.

8. The process of claim 1, wherein the insulin or insulin analog is insulin glargine or insulin lispro.

9. The process of claim 2, wherein the insulin or insulin analog is insulin glargine or insulin lispro.

10. The process of claim 5, wherein the insulin or insulin analog is insulin glargine or insulin lispro.

11. The process of claim 1, wherein the solubilization solution comprises about 15 g/L of the precursor molecules of insulin or insulin analog having incorrectly bonded cysteine bridges bodies, about 4.0 M urea, about 2.5 mM DTT, and about 315 mM ethanolamine, and has a pH at about 10.5.

12. The process of claim 1, wherein the refold solution comprises about 1.6 g/L of the precursor molecules of insulin or insulin analog having incorrectly bonded cysteine bridges, 0.38 to 0.43 M urea, 384 µM cystamine, about 0.22 to 0.28 mM DTT, and about 26.5 to 36.5 mM ethanolamine, and has a pH of about 10.5.

13. The process of claim 2, wherein the solubilization solution comprises about 15 g/L of the precursor molecules of insulin or insulin analog having incorrectly bonded cysteine bridges bodies, about 4.0 M urea, about 2.5 mM DTT, and about 315 mM ethanolamine, and has a pH at about 10.5.

14. The process of claim 2, wherein the refold solution comprises about 1.6 g/L of the precursor molecules of insulin or insulin analog having incorrectly bonded cysteine bridges, 0.38 to 0.43 M urea, 384 µM cystamine, about 0.22 to 0.28 mM DTT, and about 26.5 to 36.5 mM ethanolamine, and has a pH of about 10.5.

15. The process of claim 5, wherein the solubilization solution comprises about 15 g/L of the precursor molecules of insulin or insulin analog having incorrectly bonded cysteine bridges bodies, about 4.0 M urea, about 2.5 mM DTT, and about 315 mM ethanolamine, and has a pH at about 10.5.

16. The process of claim 5, wherein the refold solution comprises about 1.6 g/L of the precursor molecules of insulin or insulin analog having incorrectly bonded cysteine bridges, 0.38 to 0.43 M urea, 384 µM cystamine, about 0.22 to 0.28 mM DTT, and about 26.5 to 36.5 mM ethanolamine, and has a pH of about 10.5.

\* \* \* \* \*